United States Patent
Coroneo

(10) Patent No.: US 9,622,857 B2
(45) Date of Patent: Apr. 18, 2017

(54) METHOD OF MAINTAINING THE STRUCTURE OF AN OPENING IN THE ANTERIOR OR POSTERIOR CAPSULE

(76) Inventor: Minas Theodore Coroneo, Vaucluse (AU)

(\*) Notice: Subject to any disclaimer, the term of this patent is extended or adjusted under 35 U.S.C. 154(b) by 0 days.

(21) Appl. No.: 13/620,182

(22) Filed: Sep. 14, 2012

(65) Prior Publication Data

US 2013/0013061 A1 Jan. 10, 2013

Related U.S. Application Data

(62) Division of application No. 12/087,968, filed as application No. PCT/AU2007/000044 on Jan. 17, 2007, now abandoned.

(30) Foreign Application Priority Data

Jan. 17, 2006 (AU) .................. 2006900235

(51) Int. Cl.
*A61F 2/16* (2006.01)

(52) U.S. Cl.
CPC .............. *A61F 2/1694* (2013.01); *A61F 2/16* (2013.01); *A61F 2002/1696* (2015.04); *A61F 2002/16901* (2015.04); *A61F 2002/16902* (2015.04)

(58) Field of Classification Search
CPC .... A61F 2/1613; A61F 2/1648; A61F 2/1694; A61F 2002/1681; A61F 2002/1686; A61F 2002/1697; A61F 2002/16976; A61F 2/14
USPC ... 623/4.1, 6.11, 6.32, 6.34, 6.35, 6.39–6.41, 623/6.43
See application file for complete search history.

(56) References Cited

U.S. PATENT DOCUMENTS

| | | |
|---|---|---|
| 3,807,393 A | 4/1974 | McDonald |
| 4,463,458 A | 8/1984 | Seidner |
| 4,950,289 A | 8/1990 | Krasner |
| 5,026,396 A | 6/1991 | Darin |
| 5,323,788 A | 6/1994 | Silvestrini et al. |
| 5,628,795 A | 5/1997 | Langerman |
| 5,697,973 A | 12/1997 | Peyman et al. |
| 6,063,118 A | 5/2000 | Nagamoto |

(Continued)

FOREIGN PATENT DOCUMENTS

| | | |
|---|---|---|
| EP | 0478929 A1 | 4/1992 |
| FR | 2 849 592 A1 | 7/2004 |

(Continued)

OTHER PUBLICATIONS

Lanzetta, P. et al. 2002 "Use of capsular ring in phacoemulsification, indications and technique" *Indian Journal of Opthalmology* 50: 333-337.

*Primary Examiner* — Howie Matthews
(74) *Attorney, Agent, or Firm* — Knobbe, Martens, Olson & Bear, LLP

(57) ABSTRACT

A method of maintaining the structure of an opening in the anterior or posterior capsule formed by a capsulorhexis whereby a device is inserted into opening in the anterior or posterior capsule, the device having a main body including a peripheral portion and an opening therethrough, wherein the peripheral portion engages with the inside peripheral edge of the opening in the anterior or posterior capsule, wherein the device is inserted into the opening in the anterior or posterior capsule after an intraocular lens has been inserted into the capsular bag of an eye during cataract corrective surgery.

14 Claims, 2 Drawing Sheets

(56) References Cited

U.S. PATENT DOCUMENTS

| | | |
|---|---|---|
| 6,406,739 B1 | 6/2002 | LeBoeuf et al. |
| 6,966,913 B2 | 11/2005 | Israel |
| 2001/0004708 A1 | 6/2001 | Nagai |
| 2002/0128710 A1 | 9/2002 | Eggleston |
| 2002/0173846 A1* | 11/2002 | Blake et al. ............... 623/6.18 |
| 2004/0236422 A1* | 11/2004 | Zhang et al. ............... 623/6.34 |
| 2005/0187623 A1 | 8/2005 | Tassignon |
| 2006/0047339 A1* | 3/2006 | Brown ............... 623/6.13 |

FOREIGN PATENT DOCUMENTS

| | | |
|---|---|---|
| JP | 2000-237218 A2 | 9/2000 |
| WO | WO 95/15120 A1 | 6/1995 |
| WO | WO 00/21467 A1 | 4/2000 |
| WO | WO 03/022182 A1 | 3/2003 |

* cited by examiner

METHOD OF MAINTAINING THE STRUCTURE OF AN OPENING IN THE ANTERIOR OR POSTERIOR CAPSULE

FIELD OF THE INVENTION

The present invention relates to a device and method for maintaining the shape and/or position of an opening formed by a capsulorhexis in the anterior or posterior capsule of the eye.

BACKGROUND

A cataract is a condition where the lens of the eye becomes opaque ultimately leading to impaired vision. Cataracts are the main cause of blindness worldwide. Treatment consists of a surgical procedure wherein the cataract is extracted and replaced with an intraocular lens.

A central circular capsulorhexis of appropriate size and edge integrity is the key to successful cataract surgery. This is where a continuous circular incision is made in the anterior capsule that then allows for safe phacoemusification surgery and determines centration and stability of the capsular-fixated intraocular lens.

Although cataract extraction aims to remove the content of the capsular bag (the outer layer of the crystalline lens), invariably some lens epithelial cells are left behind, on the inner aspect of the lens capsule. Human capsular bags contain a large population of viable cells for many years after cataract surgery. In this environment an "after-cataract" may be formed, caused by the proliferation of lenticular epithelial cells, fibroblasts, macrophages and even iris-derived pigment cells on the lens capsule.

In order to counteract this problem, technologies have been developed for removing the lens epithelial cells, however these techniques cannot remove other cell types that can invade the capsule from the ocular aqueous humour circulation or iris.

As a result, these various cell populations participate in a fibrotic process whereby the anterior capsule opening after capsulorhexis gradually constricts to some extent. This contraction (or phimosis) of the anterior capsule opening can occur excessively in children, young adults and in certain pathological states—including diabetes, retinitis pigmentosa, pseuodexfoliation of the lens capsule, myotonic dystrophy, glaucoma and uveitis.

At present, in routine surgery, the aim is to create a capsulorhexis of appropriate size, typically 5.5 mm for an intraocular lens with an optic diameter of 6 mm. It is thought that this symmetrical overlap of anterior capsule over the periphery of the intraocular lens "shrink-wraps" the intraocular lens.

As phimosis occurs, the encroaching anterior capsule can be incised using a Yag laser or by open operation. This can relieve the capsule contraction but can also result in complications such as retinal detachment, macular oedema, lens dislocation and presentation of vitreous into the anterior eye. If the capsulorhexis is made larger than this (to "overcompensate" for future phimosis), the anterior and posterior leaves of the capsule can fuse in an asymmetric fashion, resulting in "peapoding" where the intraocular lens is displaced away from the visual axis, resulting in reduced vision.

Removal of anterior subcapsular epithelial cells by aspiration helps maintain the size of the capsulorhexis opening (6 month follow up) but it is uncertain as to whether this prevents capsule contraction syndrome in the longer term In certain cases, the fibrosis is so extensive that the anterior lens surface is covered over, resulting in marked reduction in vision. As the lens capsule is attached to the inner wall of the eye (over the ciliary body) by delicate zonular fibres, the fibrotic process can result in the zonular support being pulled off the ciliary body and the whole of the capsular bag containing the intraocular lens can dislocate into the vitreous body.

The capsular tension ring (CTR) was originally introduced to reinforce the zonule in eyes with zonular dehiscence and to prevent capsular phimosis in eyes at risk for postoperative capsular shrinkage. Yet despite insertion of CTR's capsule phimosis can still occur.

Accordingly, the present invention seeks to provide a device and method for maintaining the structural integrity of anterior capsule opening formed as a result of a capsulorhexis and reduce the risk of phimosis occurring after cataract surgery.

SUMMARY OF THE INVENTION

According to one aspect the present invention provides a device for maintaining the shape and/or position of an opening formed by a capsulorhexis in the anterior or posterior capsule, the device having a main body including a peripheral portion and an opening therethrough, wherein the peripheral portion engages with the inside peripheral edge of the opening in the anterior or posterior capsule.

Preferably, the peripheral portion of the device is substantially circular in shape whereby the device is in the form of a ring.

Preferably, the peripheral portion of the device includes a groove whereby in use the inside peripheral edge of the opening in the anterior or posterior capsule is positioned inside the groove. Preferably, the groove is around the entirety of the peripheral portion of the device.

According to one embodiment, the device may be formed from a flexible material that allows the device to be deformed sufficiently to be inserted into and engaged within the inside peripheral edge of the opening in the anterior or posterior capsule, whilst still providing sufficient rigidity to maintain the shape and/or position of the opening. The flexible material may be chosen from any suitable biocompatible material, such as for example surgical grade rubber or plastic. Preferably, the device is formed from a material that reduces or minimizes glare that may be caused by the device, such as for example frosted and/or pigmented material.

According to another embodiment, the peripheral portion of the device moves between a collapsed state and an assembled state, whereby the device is inserted into the opening in the anterior or posterior capsule in the collapsed state. The device may then be assembled within the opening such that the peripheral portion engages with the inside peripheral edge of the opening in the anterior or posterior capsule. Preferably the device moves between a folded and an unfolded state by means of a hinge. Optionally in the collapsed state, the peripheral portion may detach at one or more points along its length to form an open state wherein the peripheral portion can then reattach and form a closed state when the device is in the assembled state.

According to one embodiment, the device is adapted to hold an intraocular lens (IOL). Preferably, the peripheral portion includes an inside surface adapted to hold the IOL. The inside surface may include a groove or channel whereby in use the periphery of the IOL is positioned inside the groove or channel thereby holding the IOL within the opening of the device.

In another embodiment, the peripheral portion includes one or more apertures through which correspondingly spaced protruding members on the periphery of an IOL engage for holding the IOL within the opening of the device. Preferably, the IOL is held within the opening of the device by three or more protruding members engaging with their corresponding apertures. For a toric IOL, the apertures of the peripheral portion allow for orientation of the IOL for correct axis alignment.

According to another aspect the present invention provides a method of maintaining the structure of an opening in the anterior or posterior capsule formed by a capsulorhexis whereby a device is inserted into opening in the anterior or posterior capsule, the device having a main body including a peripheral portion and an opening therethrough, wherein the peripheral portion engages with the inside peripheral edge of the opening in the anterior or posterior capsule.

Preferably, the device is inserted into the opening in the anterior or posterior capsule after an intraocular lens has been inserted into the capsular bag during cataract corrective surgery. Preferably, the device remains engaged with the opening in the anterior or posterior capsule for an indefinite period of time after cataract corrective surgery, to prevent or minimise phimosis of the opening in the anterior or posterior capsule. More preferably, the device remains engaged with the opening in the anterior or posterior capsule permanently after cataract corrective surgery.

Preferably, the device is inserted into the opening in the anterior or posterior capsule with the assistance of an applicator means, such as for example an applicator tool that allows a surgeon to handle and correctly position the device in the opening in the anterior or posterior capsule.

BRIEF DESCRIPTION OF THE DRAWINGS

The present invention will become better understood from the following detailed description of a preferred but non-limiting embodiment thereof, described in connection with the accompanying drawings, wherein.

DETAILED DESCRIPTION OF THE INVENTION

Figure 1:
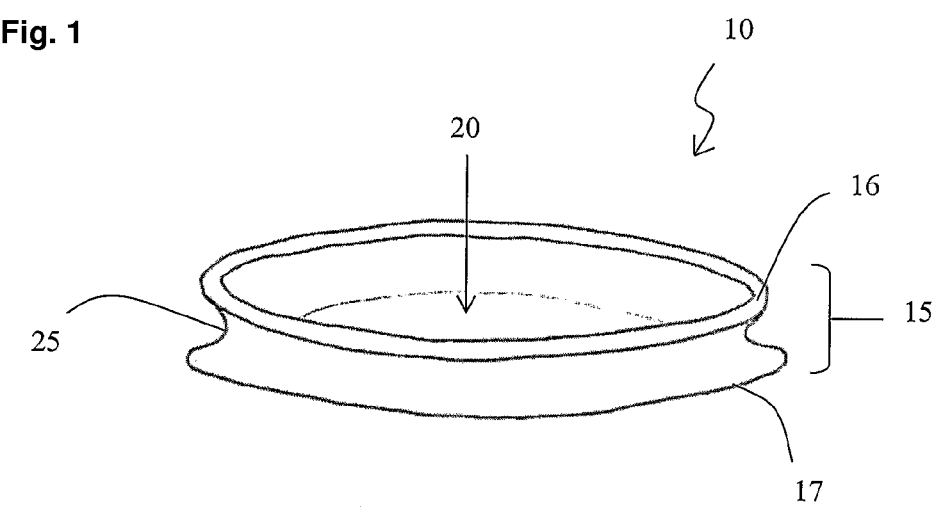
FIG. 1 is an isometric view of a device in accordance with one embodiment of the present invention from above and one side.

The device of the present invention is preferably designed to be inserted into an anterior capsule opening formed by a capsulorhexis, in order to maintain the shape and/or position of the opening over time. The device is preferably composed of a biocompatible material and has the appearance of an inverted tyre wherein the device has a groove in its outer diameter into which the peripheral edge of the opening of the anterior capsule sits.

A preferable diameter of the device would be 4-8 mm—the "functional" diameter i.e. at the depths of the groove would be 5-5.5 mm to accommodate an "ideal" 5.5 mm opening of the anterior capsule formed from a capsulorhexis. A number of sizes would be available, as an opening of "ideal" size is not always possible. As the opening can be stretched as much as 62%, procedures involving the device of the present invention could aim for a slightly smaller opening size of 4.5-5 mm wherein the device would be "squeezed" into the opening, so that the fit is snug if a 5.5 mm diameter device is used.

Preferably, the device is designed that there be 1-3 mm of overlap, so that the device engages securely with the peripheral edge of the opening of the anterior capsule and is held securely in place preventing the possibility of the device being expelled from the opening due to phimosis.

It is preferable that the device of the present invention is flexible to a certain degree, and thus could be inserted in the form of a complete ring though a standard 3 mm cataract surgery wound. Alternatively, it could be injected into the eye as an incomplete ring and once in position, the ring is closed by a hinged segment (see Graether U.S. Pat. Nos. 5,267,553 & 5,634,884). Preferably, the hinged segment allows for some adjustment to the overall diameter of the device by means of a number of attachment points.

Once in place within the opening of the anterior capsule, the device of the present invention would ensure that capsule phimosis cannot occur. The fibrotic forces would be redistributed in the lens capsule, but as the anterior capsule opening can now no longer contract, it would prevent forces on the zonular apparatus and therefore prevent dislocation of the intraocular lens. As an asymmetric opening in the anterior capsule from capulorhexis can be associated with asymmetry of contraction forces (and can contribute to "pea-poding"), the device of the present invention will make the opening more symmetrical and facilitate long term intraocular lens centration. The device according to the present invention may also include a coupling means to which a drug for delivery may be attached. Actives that may desirably be delivered intraocularly in this manner include anti-inflammatory agents such as steroids or non-steroidal agents, antimicrobial agents such as antibiotics, antiviral or anti-fungal agents antiglaucoma agents, agents to inhibit lens cell proliferation such as 5-fluorouracil or mitomycin c, neuroprotectants or inhibitors of neovascularization.

The device according to the invention can be used to maintain the shape and/or position of an opening formed by a capsulorhexis during cataract corrective surgery in humans, and in animals such as cats, dogs, horses or any other animal requiring cataract corrective surgery and in which a capsulorhexis is performed.

A consequence of placement of the capsulorhexis ring is that it can be utilized to hold an intraocular lens in a setting where the posterior capsule has been inadvertently ruptured. Posterior capsule rupture is a recognized complication of cataract surgery and may be associated with poor outcomes, some of which may be due to unsatisfactory location of the intraocular lens. In these circumstances, the intraocular lens can be placed in the anterior chamber or commonly, behind the iris, with the intraocular lens haptics located in the ciliary sulcus. This location may be unstable and the intraocular lens can migrate away from the visual axis. A technique described by Dr Howard V. Gimbel of Canada, utilizes sulcus fixation with the intraocular lens optic being pushed posteriorly through the intact capsulorhexis, thus providing "lens optic capture". This technique relies in part on the capsulorhexis being the correct size. By creating a flexible intraocular lens of appropriate diameter having protruding members spaced on the periphery of the intraocular lens optic and providing corresponding apertures in the peripheral portion of the device of the present invention, an intraocular lens can be accurately and reliably held within the opening of the device.

During standard cataract corrective surgery, a wound is created in the wall of the eye. Capsulorhexis is performed resulting in an opening in the anterior capsule. The crystalline lens substance is then removed through the opening by phacoemulsification afterwhich an intraocular lens is inserted into the capsular bag. Facilitating viscoelastic fluids are then removed, steroid and antibiotic injections are typically given and the eye is bandaged. The insertion of the device of the present invention would be an additional step during the aforementioned surgical procedure, with insertion occurring after the intraocular lens has been inserted into the capsular bag.

Particularly in paediatric cataract (as well as some of the pathological conditions mentioned above), there can be excessive fibrosis of the posterior capsule. Some surgeons perform a primary posterior capsulorhexis, typically smaller in diameter than the anterior capsulorhexis. This too can phimose. Accordingly, the device of the present invention can be used both for maintaining the shape and/or position of an opening in the anterior and posterior capsule.

It is believed the device of the present invention may reduce an unwanted type of glare known as dysphotopsia. In this phenomenon, peripheral sidelight is focused by the anterior eye on the peripheral optics of the intraocular lens, resulting in a series of foci on the peripheral nasal retina. This results in annoying images in the patient's temporal field of vision. In fact, eccentric capsulorhexis has been reported to be associated with postoperative dysphotopsia. The device of the present invention would potentially reduce the amount of sidelight striking the periphery of the intraocular lens. In particular, the anterior aspect of the device could be extended to protrude anteriorly for 1-2 mm to minimize any gap that may exist between the anterior capsule and posterior iris as this gap may allow a pathway of peripheral light that contributes to dysphotopsia.

Referring to FIG. 1, there is shown a device 10 in accordance with an embodiment of the present invention. The device 10 consists of a main body portion in the form of a ring with a hole or opening 20 passing through the main body portion. The main body portion includes a peripheral portion 15 that further includes a groove 25 passing right around the entirety of the peripheral portion 15. Due to the structure of the groove around the peripheral portion of the device two retaining flanges 16, 17 above and below the groove are provided.

The device 10 would be typically composed of a flexible bio-compatible material that maintains a degree of rigidity when inserted into the opening 30 formed by a capsulorhexis in the anterior or posterior capsule. But which at the same time would allow the device to be squeezed into and fitted within the opening of the anterior capsule.

Figure 2:
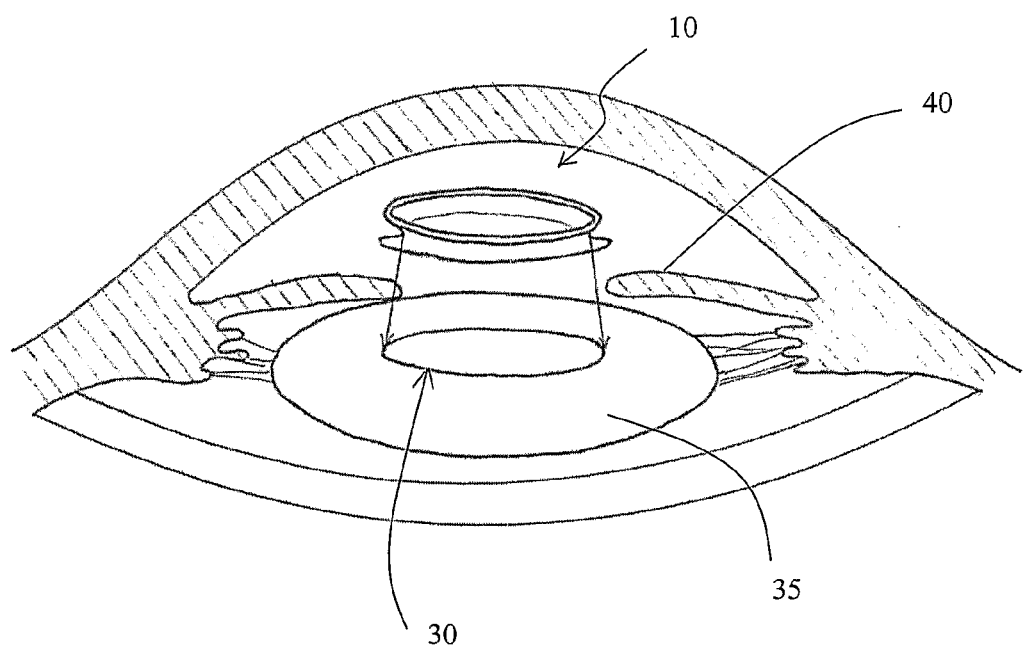
FIG. 2 is a schematic view of a device in accordance with one embodiment of the present invention together with a diagrammatical representation of an eye including a capsulorhexis.

Referring now to FIG. 2, there is shown the device 10 about to be inserted into an opening 30 formed by a capsulorhexis of an anterior capsule 35. The opening 30 would normally be in a range of 5.0-5.5 mm in diameter.

During cataract corrective surgery, a capsulorhexis is performed on an anterior capsule providing an opening 30 through which the cataract affected lens can be removed by a phacoemusification. After the cataract affected lens is removed, an intra-ocular lens is inserted within the capsule bag 35. At this point, the device 10 may be inserted into the opening 30 in the anterior capsule whereby the peripheral edge of the opening 30 is fitted within the groove 25 of the device 10 and retained in place by retaining flanges 16, 17. In this manner, the device 10 is securely engaged within the opening 30 of the anterior capsule.

The device 10 is left in place within the opening 30 of the anterior capsule maintaining the position and/or shape of the opening in the anterior capsule preventing or minimising phimosis and allowing a passage for light to pass through the intraocular lens located in the capsule bag 35.

Figure 3:
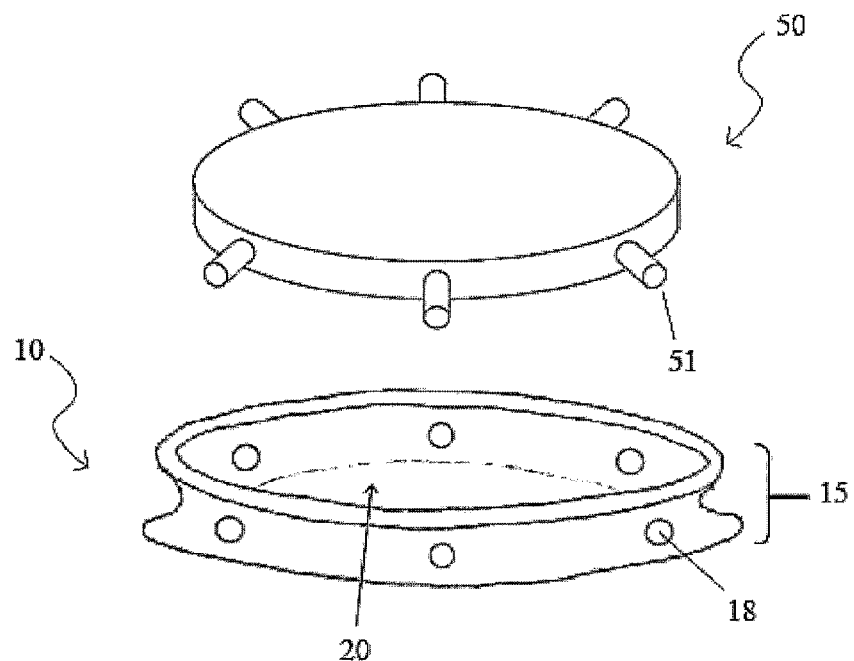
FIG. 3 is an isometric view of a device in accordance with one embodiment of the present invention together with an isometric view of suitably configured IOL for insertion into the opening of the device, from above and one side.

Referring now to FIG. 3, there is shown a device 10 in accordance with an embodiment of the present invention having a plurality of evenly spaced apertures 18 in the peripheral portion 15 of the device. In the illustrated embodiment, the evenly spaced apertures 18 are circular. Also shown is an IOL 50 having a plurality of evenly spaced protruding cylindrical members 51 corresponding in number and positioning to the apertures 18 of the device 10. In use, the protruding members 51 of the IOL 50 are aligned and engaged with corresponding apertures 18 of the device 10, thereby securing the IOL within the opening 20 of the device.

Finally, it can be understood that the inventive concept in any of its aspects can be incorporated in many different constructions and/or methods so that the generality of the preceding description is not to be superseded by the particularity of the attached figures. Various alterations, modifications and/or additions may be incorporated into the various constructions and arrangements of parts without departing from the spirit or ambit of the invention.

What is claimed is:

1. A method of maintaining the structure of an opening in the anterior capsule formed by a capsulorhexis comprising:
   (a) creating an opening in the anterior of a capsular bag by capsulorhexis;
   (b) inserting an intraocular lens (IOL) through the opening completely into the capsular bag; and
   (c) separately inserting a device into the opening in the anterior capsule after the intraocular lens is completely inserted into the capsular bag, the device comprising an annular shaped main body including a peripheral portion and an opening therethrough, wherein the peripheral portion engages with the inside peripheral edge of the opening in the anterior capsule, and wherein an anterior aspect of the device protrudes anteriorly for 1-2 mm completely around the opening in the anterior capsule to extend between the anterior capsule and an iris, thereby minimizing any gap that may exist between the anterior capsule and the iris and blocking peripheral light towards a periphery of the intraocular lens, so that dysphotopsia is minimized.

2. The method according to claim 1, wherein the device remains engaged with the opening in the anterior capsule for an indefinite period of time after cataract corrective surgery.

3. The method according to claim 1, wherein the device remains engaged with the opening in the anterior capsule permanently after cataract corrective surgery.

4. The method according to claim 1, wherein the device is inserted into the opening in the anterior capsule with the assistance of an applicator means.

5. The method according to claim 1 performed in a human or other animal requiring cataract corrective surgery.

6. The method according to claim 1, wherein the peripheral portion of the device is circular in shape.

7. The method according to claim 1, wherein the peripheral portion comprises a groove whereby in use the inside peripheral edge of the opening in the anterior capsule is positioned inside the groove.

8. The method according to claim 7, wherein the groove surrounds the entirety of the peripheral portion of the device.

9. The device according to claim 1, wherein the device is formed from a surgical grade rubber or plastic.

10. The method according to claim 9, wherein the surgical grade rubber or plastic is biocompatible.

11. The method according to claim 9, wherein the surgical grade rubber or plastic reduces or minimizes glare.

12. The method according to claim 1, wherein the device moves between a collapsed state and an assembled state.

13. The method according to claim 1, wherein the device moves between a folded and an unfolded stated by means of a hinge.

14. The method according to claim 12, wherein in the collapsed state the peripheral portion may detach at one or more points along its length to form an open state wherein the peripheral portion can then reattach and form a closed state when the device is in the assembled state.

\* \* \* \* \*